United States Patent
Fischvogt et al.

(10) Patent No.: US 9,554,825 B2
(45) Date of Patent: *Jan. 31, 2017

(54) ACCESS ASSEMBLY

(71) Applicant: Covidien LP, Mansfield, MA (US)

(72) Inventors: Gregory Fischvogt, Hamden, CT (US); Sally Carter, Nashua, NH (US)

(73) Assignee: Covidien LP, Mansfield, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/630,137

(22) Filed: Feb. 24, 2015

(65) Prior Publication Data
US 2015/0182254 A1    Jul. 2, 2015

Related U.S. Application Data

(63) Continuation of application No. 12/416,460, filed on Apr. 1, 2009, now Pat. No. 8,968,251.

(Continued)

(51) Int. Cl.
     *A61B 17/34*      (2006.01)
     *A61M 39/02*      (2006.01)

(52) U.S. Cl.
     CPC ...... *A61B 17/3462* (2013.01); *A61M 39/0247* (2013.01); *A61B 2017/3445* (2013.01);
(Continued)

(58) Field of Classification Search
     CPC ............. A61M 2039/0686; A61M 2039/0626; A61M 39/06; A61M 2039/0279; A61M 39/0613; A61M 39/02; A61M 2039/027; A61M 2039/0054; A61M 2039/0258; A61M 2039/0264; A61M 39/0247; A61B 17/3462; A61B 2017/3445; A61B 2017/3449; A61B 2017/346; A61B 2017/3466

See application file for complete search history.

(56) References Cited

U.S. PATENT DOCUMENTS

| | | |
|---|---|---|
| 5,000,745 A | 3/1991 | Guest et al. |
| 5,009,391 A | 4/1991 | Steigerwald |

(Continued)

FOREIGN PATENT DOCUMENTS

| | | |
|---|---|---|
| DE | 29700761 U1 | 5/1998 |
| FR | 2710270 A1 | 3/1995 |

OTHER PUBLICATIONS

European Search Report, Application No. 09 25 1222, dated Aug. 7, 2009.

*Primary Examiner* — Bhisma Mehta
*Assistant Examiner* — Brandy S Lee

(57) ABSTRACT

An access assembly is provided. The access assembly includes an access member defining a central longitudinal axis and having a longitudinal opening therethrough for reception and passage of surgical instrument, the access member dimensioned for positioning within tissue to provide access to underlying tissue, and first and second seal members mounted to the access member in juxtaposed relation, the first seal member defining an opening therethrough, the second seal member defining an elongated arcuate passage, wherein the first and second seal members are adapted for rotational movement about the central longitudinal axis whereby the opening of the first seal member is axially alignable with the elongated arcuate passage of the second seal member to permit reception and passage of the surgical instrument in substantial sealed relation therewith, the first and second seal members further adapted for relative rotational movement whereby the first seal member is capable of rotating relative to the second seal member during manipulation and traversal of the surgical instrument through the elongated arcuate passage of the second seal member to maintain the substantial sealed relation about the instrument.

18 Claims, 8 Drawing Sheets

Related U.S. Application Data

(60) Provisional application No. 61/053,064, filed on May 14, 2008.

(52) U.S. Cl.
CPC ............... *A61B 2017/3449* (2013.01); *A61B 2017/3466* (2013.01); *A61M 2039/0264* (2013.01); *A61M 2039/0279* (2013.01)

(56) References Cited

U.S. PATENT DOCUMENTS

| | | | |
|---|---|---|---|
| 5,104,389 A | | 4/1992 | Deem et al. |
| 5,167,637 A | | 12/1992 | Okada et al. |
| 5,176,652 A | | 1/1993 | Littrell |
| 5,207,649 A | | 5/1993 | Aruny |
| 5,211,370 A | | 5/1993 | Powers |
| 5,211,633 A | | 5/1993 | Stouder, Jr. |
| 5,350,364 A | | 9/1994 | Stephens et al. |
| 5,389,081 A | | 2/1995 | Castro |
| 5,409,463 A | | 4/1995 | Thomas et al. |
| 5,443,452 A | | 8/1995 | Hart et al. |
| 5,643,227 A | | 7/1997 | Stevens |
| 6,086,570 A | * | 7/2000 | Aboul-Hosn ..... A61M 39/0606 251/149 |
| 6,099,505 A | | 8/2000 | Ryan et al. |
| 6,610,031 B1 | | 8/2003 | Chin |
| 7,172,580 B2 | | 2/2007 | Hruska et al. |
| 2004/0064100 A1 | | 4/2004 | Smith |
| 2005/0148823 A1 | * | 7/2005 | Vaugh ................ A61B 17/0293 600/206 |
| 2006/0084842 A1 | | 4/2006 | Hart et al. |
| 2006/0241651 A1 | | 10/2006 | Wilk |

\* cited by examiner

ACCESS ASSEMBLY

CROSS REFERENCE TO RELATED APPLICATION

The present application is a continuation of U.S. patent application Ser. No. 12/416,460, filed Apr. 1, 2009, which claims the benefit of and priority to U.S. Provisional Patent Application Ser. No. 61/053,064, filed on May 14, 2008, the entire contents of which are incorporated herein by reference.

BACKGROUND

Technical Field

The present disclosure relates to assemblies for accessing a body cavity, and more particularly, the disclosure relates to an access assembly for receiving more than one instrument therethrough, and for manipulating the instruments relative to each other.

Background of Related Art

Trocars and other access assemblies are used by surgeons to operate on a patient without having to create large incisions that may become infected and may cause major scaring. Access assemblies are known in the art, as are the instruments inserted therethrough for operating within the body cavity. Typically, an access assembly includes a housing configured receiving an instrument, and a tubular member or cannula affixed to the housing and configured for insertion into a body cavity. These assemblies generally include at least one seal mounted within the housing and/or cannula to prevent the escape of insufflation gas.

Tradition access assemblies are configured to receive a single instrument. Therefore, a surgeon must use multiple access assemblies to complete an operation requiring the simultaneous use of more than one instrument. Inserting multiple access assemblies into a patient increases the length of the procedure, as well as increases the potential sites for infection and/or complications.

Therefore, it would be beneficial to have an access assembly capable of receiving more than one instrument. It would further be beneficial if, once received, the instruments could be manipulated relative to one another.

SUMMARY

An access assembly is provided. The access assembly includes an access member defining a central longitudinal axis and having a longitudinal opening therethrough for reception and passage of surgical instrument, the access member dimensioned for positioning within tissue to provide access to underlying tissue, and first and second seal members mounted to the access member in juxtaposed relation, the first seal member defining an opening therethrough, the second seal member defining an elongated arcuate passage, wherein the first and second seal members are adapted for rotational movement about the central longitudinal axis whereby the opening of the first seal member is axially alignable with the elongated arcuate passage of the second seal member to permit reception and passage of the surgical instrument in substantial sealed relation therewith, the first and second seal members further adapted for relative rotational movement whereby the first seal member is capable of rotating relative to the second seal member during manipulation and traversal of the surgical instrument through the elongated arcuate passage of the second seal member to maintain the substantial sealed relation about the instrument.

In the access assembly, the opening of the first seal member and the elongated arcuate passage of the second seal member are radially spaced from the central longitudinal axis. The elongated arcuate passage is arranged to at least partially circumscribe the central longitudinal axis. Each of the first and second seal members includes the opening and the elongated arcuate passage whereby the opening of the second seal member is axially alignable with the elongated arcuate passage of the first seal member to permit reception and passage of a second surgical instrument in substantial sealed relation therewith.

The access assembly may include a third seal member mounted to the access member in juxtaposed relation with the second seal member, the third seal member including the opening and the elongated arcuate passage therethrough, the third seal member adapted for rotational movement about the central longitudinal axis. The third seal member may be adapted for rotational movement relative to at least one of the first and second seal members.

BRIEF DESCRIPTION OF THE DRAWINGS

The foregoing summary, as well as the following detailed description will be better understood when read in conjunction with the appended figures. For the purpose of illustrating the present disclosure, a preferred embodiment is shown. It is understood, however, that the present disclosure is not limited to the precise arrangement and instrumentalities shown.

DETAILED DESCRIPTION

Figure 1:
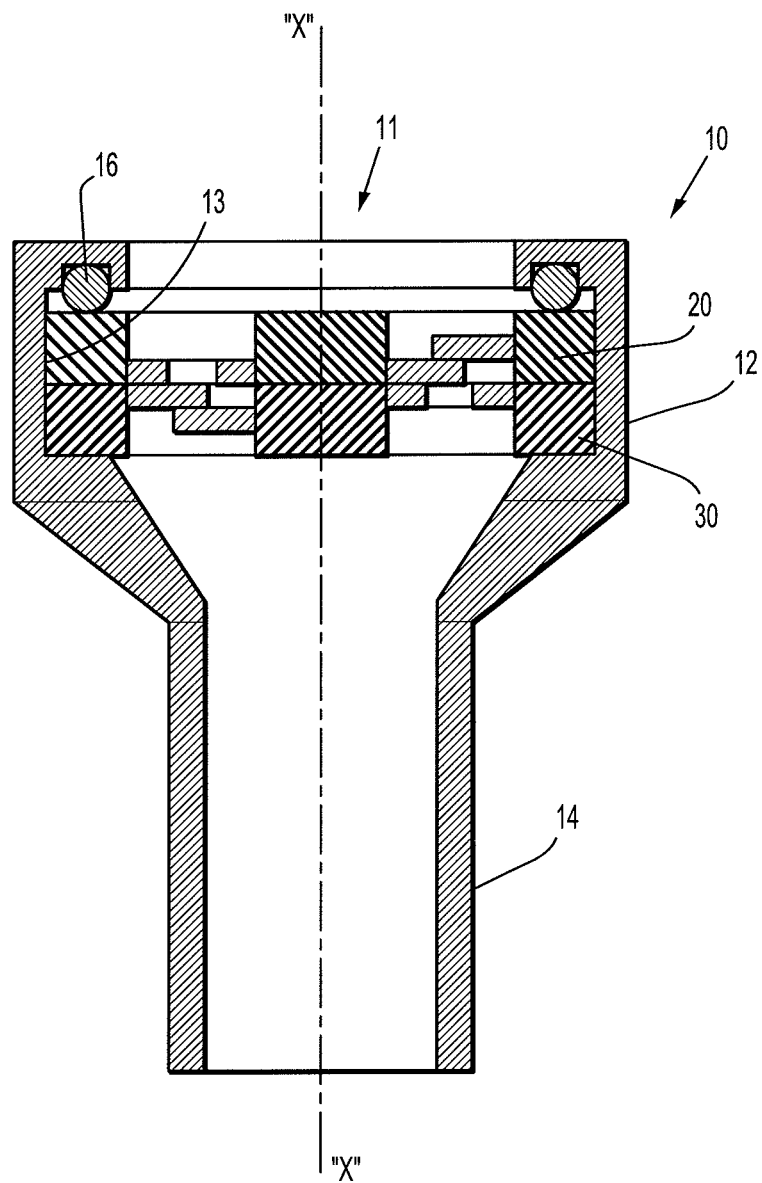
FIG. 1 is a cross-sectional side view of an access assembly according to embodiment of the present disclosure.

Referring now to the drawings wherein like reference numerals illustrate similar components throughout the several views. As shown in the drawings and as described throughout the following description, as is traditional when referring to relative positioning on an object, the term "proximal" refers to the end of the apparatus which is closer to the user and the term "distal" refers to the end of the apparatus which is further from the user.

Figure 5:
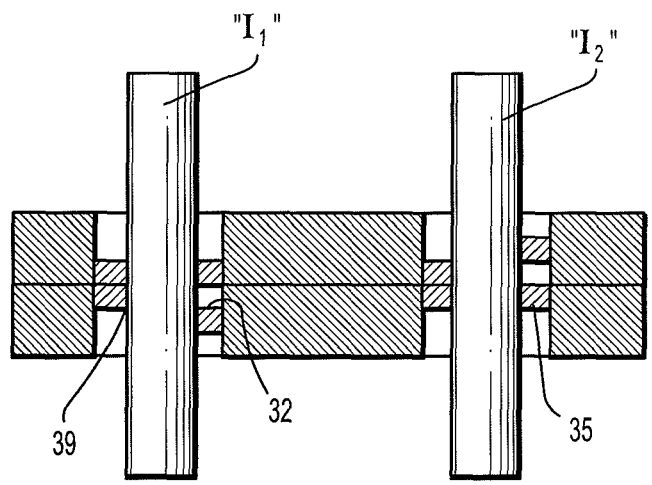
FIG. 5 is a cross-sectional side view of the seal members of FIG. 4 receiving an endoscopic instruments therethrough.
Figure 6:
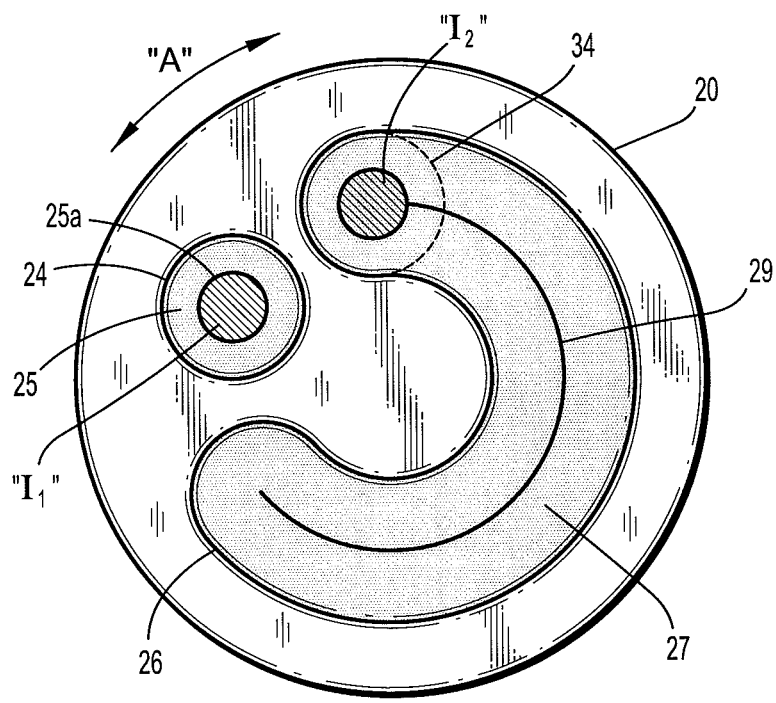
FIG. 6 is a top view of the seal members of FIGS. 4 and 5 including endoscopic instruments inserted therethrough.
Figure 7:
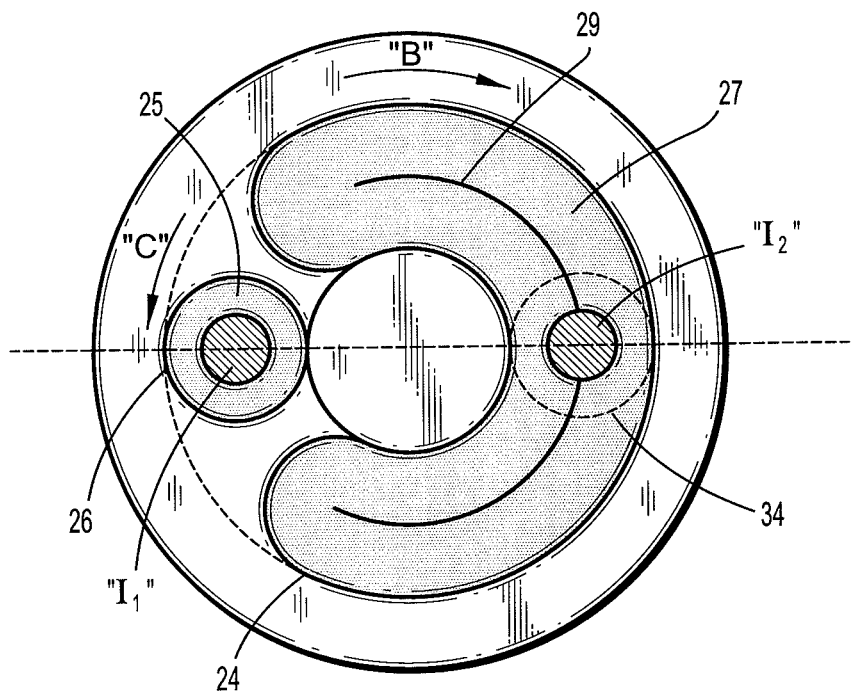
FIG. 7 is a top view of the seal members of FIGS. 4-6 as the first and second seal members are rotated relative to each other.

With reference initially to FIG. 1, an embodiment of an access assembly in accordance with the aspects of the present disclosure is shown generally as access assembly or member 10. Access assembly 10 includes a housing 12 and a cannula 14 extending from housing 12. Access assembly 10 defines a longitudinal passageway 11 having a central axis "X". Access assembly 10 is configured for receiving one or more endoscopic instruments "I1", "I2" (FIG. 5) therethrough.

Still referring to FIG. 1, housing 12 defines a cylindrical cavity 13 for receiving a first and second seal member 20, 30, although it is envisioned that cavity 13 may be configured to receive any number of seal members. As will be described in further detail below, seal members 20, 30 are configured to cooperatively receive one or more endoscopic instruments "I1", "I2" in a sealing manner. Seal members 20, 30 are further configured to permit the manipulation of endoscopic instruments "I1", "I2" relative to one another and relative to housing 12. Cylindrical cavity 13 is sized and dimensioned such that seal members 20, 30 may rotate freely about axis "X" relative to housing 12 and relative to each other. Seal members 20, 30 are sealed within housing 12 by an O-ring 16 or other suitable sealing means.

Figure 2:
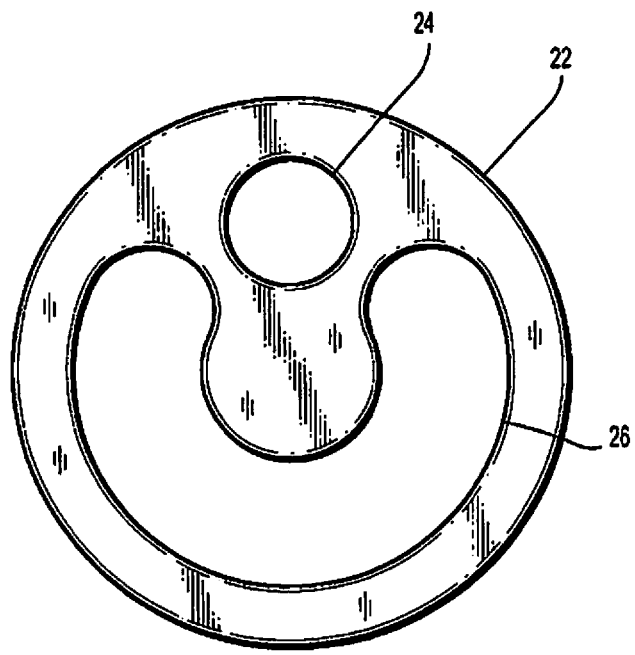
FIG. 2 is a top view of a seal member of the access assembly of FIG. 1.

Seal members 20, 30 will now be described with reference to FIGS. 2 and 3. Seal members 20, 30 are substantially identical, and therefore will only be described as relates to seal member 20. Referring initially to FIG. 2, seal member 20 includes a substantially circular base member 22 defining an opening 24 radially spaced from axis "X" (FIG. 1) and an elongated arcuate slot 26 radially spaced from and at least partially circumscribing about central axis "X". Opening 24 and slot 26 are sized and dimensioned to receive endoscopic instruments "I1", "I2" therethrough. Arcuate slot 26 defines an elongated arcuate passage extending through an arc "m" which subtends an angle "k", which, in embodiments, may be greater than 90° with respect to the central longitudinal axis "X", and, in some embodiments, may be greater than 180° with respect to the axis "X".

Figure 3:
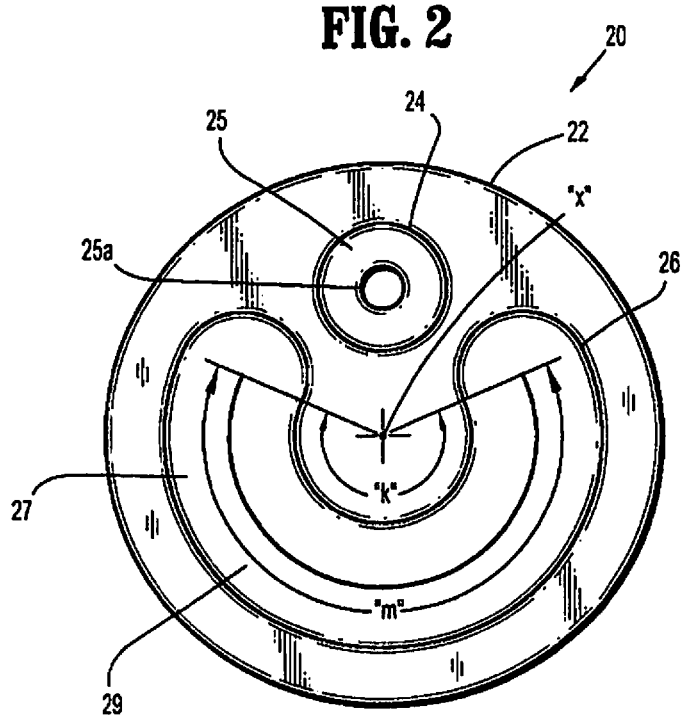
FIG. 3 is a top view of the seal member of FIG. 2 including seal members.
Figure 4:
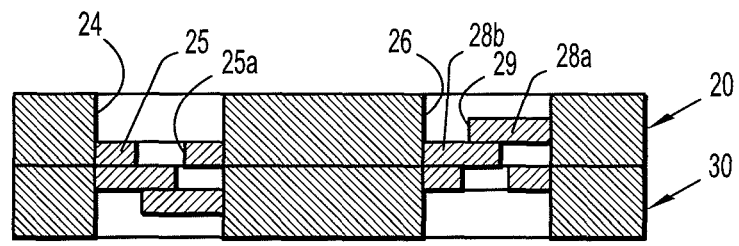
FIG. 4 is a cross-sectional side view of the seal members of the access assembly of FIG. 1.

Turning now to FIG. 3, seal member 20 includes a first seal element 25 secured within opening 24. Seal member 20 further includes a second seal element 27 secured within slot 26. Each of first and second seal elements 25, 27 are configured to receive endoscopic instrument "I1", "I2", respectively, in a sealing manner. First seal element 25 includes a flat flexible ring defining an opening 25a. First seal element 25 is configured to stretch in order to accommodate an endoscopic instrument "I1" in a sealing manner. Alternatively, or in addition, first seal element 25 may define a zero-closure seal such that opening 24 is sealed in the absence of endoscopic instrument "I". Second seal element 27 includes first and second over-lapping flexible members 28a, 28b (FIG. 4). First and second over-lapping members 28a, 28b define a slit 29 extending substantially the length of slot 26 for reception of endoscopic instrument "I2".

With reference now to FIGS. 4-7, operation of access assembly 10 will be described. As discussed above, although the following description will relate only to first and second seal members 20, 30, it is envisioned that access assembly 10 may be modified to accommodate three or more seal members. Initially first seal member 20 is positioned adjacent to second seal member 30 such that opening 24 of first seal member 20 is in vertical alignment with a slot 36 formed in seal member 30. In this manner, when a first endoscopic instrument "I1" is inserted through first seal element 25 of first seal member 20 instrument "I1" also passes through a second seal element 37 of second seal member 30. As will be discussed in further detail below, the configuration of first and second seal elements 25, 37 of first and second seal members 20, 30, respectively, increases the integrity of the seal about endoscopic instrument "I1", thereby reducing the amount of insufflation gas that may escape through access assembly 10. This is particularly important as endoscopic instrument "I1" is manipulated within access assembly 10 and also as endoscopic instrument "I1" is manipulated relative to endoscopic instrument "I2". First seal element 25 and second seal element 37 operate together to reduce cat-eyeing or other deformation of seal elements 25, 37 during manipulation of endoscopic instrument "I1" that would otherwise compromise the integrity of seal elements 25, 37 individually.

Still referring to FIGS. 4-7, a second endoscopic instrument 12" may be received through slot 26 of seal element 27 and passes through opening 25a of first seal element 25. Thus, second endoscopic instrument "I2" is also received through a double seal for increased integrity of the seal. Once received through access assembly 10 in the manner described above, first and second endoscopic instrument "I1", "I2" may be rotated together with respect to housing 12 (FIG. 1). In this manner, first and second seal members 20, 30 rotate as one, as indicated by arrow "A" in FIG. 6, within cavity 13 (FIG. 1) of access assembly 10. Additionally, first and second endoscopic instrument "I1", "I2" may be manipulated relative to each other within access assembly 10. In this manner, first and second seal members 20, 30 rotate relative to each other, as indicated by arrow "B" and "C" in FIG. 7, within cavity 13 of access assembly 10. A lubricant (not shown) may be provided between first and second seal members 20, 30 to reduce the friction therebetween and to permit free rotation thereof. The configuration of first and second seal elements 25, 35, 27, 37 of first and second seal members 20, 30, respectively, also permit first and second endoscopic instrument "I1", "I2" to be individually manipulated. In this manner, first and second endoscopic instruments "I1" 12" may be moved in any direction relative to each other and to housing 12 (FIG. 1).

Figure 8:
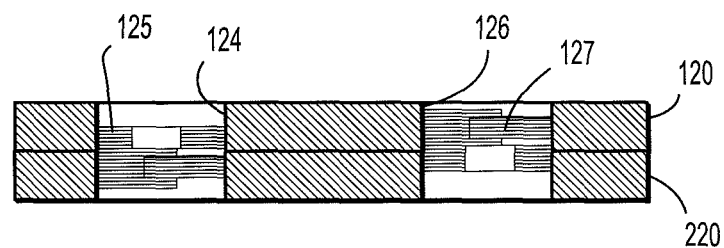
FIG. 8 is a cross-sectional side view of an alternate embodiment of seal members according to the present disclosure.

Turning now to FIG. 8, alternate embodiment of first and second seal members 20, 30 are shown generally as first and second seal members 120, 130. First and second seal members 120, 130 are substantially similar to first and second seal member 20, 30 and will only be described as relates to the differences therebetween. First and second seal member 120, 130 will be described as relates to first seal member 120. First seal member includes an opening 124 having first seal element 125 and a slot 126 including a second seal element 127. First and second seal elements 125, 127 include bristles for receiving a first and second endoscopic instruments "I1", "I2" therethrough in a sealing manner. Alternatively, the bristles may be replaced by tubular members (FIG. 9).

Figure 9:
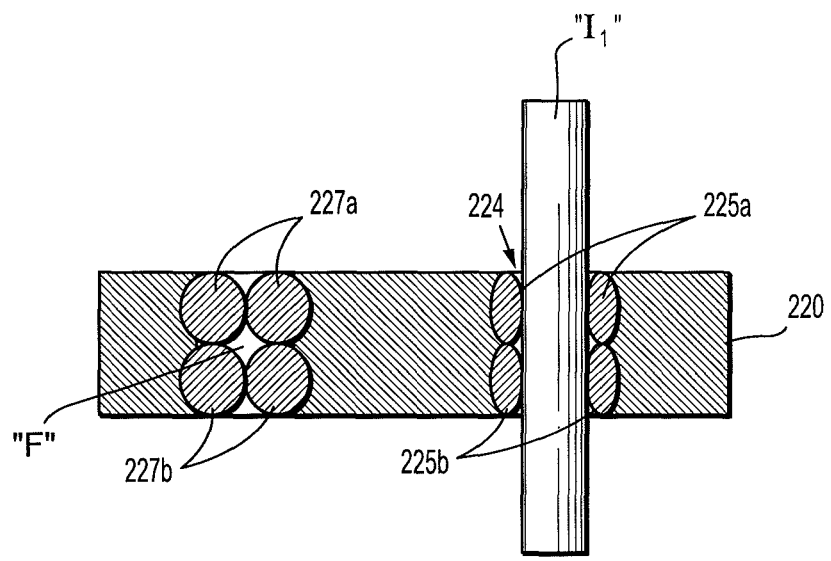
FIG. 9 is a cross-sectional side view of an alternate embodiment of a seal member according to the present disclosure.

Turning to FIG. 9, an alternate embodiment of first and second seal elements 25, 27 are shown generally as first and second seal elements 225, 227. First and second seal elements 225, 227 include a pair of tubular bumpers 225a, 225b, 227a, 227b, respectively. The operation of tubular bumpers 225a, 225b, 227a, 227b will be described as relates to tubular bumpers 225a, 225b. Tubular bumpers 225a, 225b are vertically spaced apart within opening 224 of seal member 220. Tubular members 225a, 225b are sized and dimensioned such that opening 224 is sealed in the absence of an endoscopic instrument "I1" being inserted therethrough. Tubular members 225a, 225b are further configured to received an endoscopic instrument "I1" therethrough in a sealing manner. Tubular bumpers 225a, 225b deform to accommodate the passage of endoscopic instrument "I1" through opening 224 in a sealing manner. A fluid "F" may be included between tubular bumpers 225a, 225b to increase the integrity of the seal around endoscopic instrument "I1".

Alternative seal members and seal elements for access assembly 10 will now be described in detail with reference to FIGS. 10-15. Throughout the following description, similar elements will be identified with like numerals.

Figure 10:
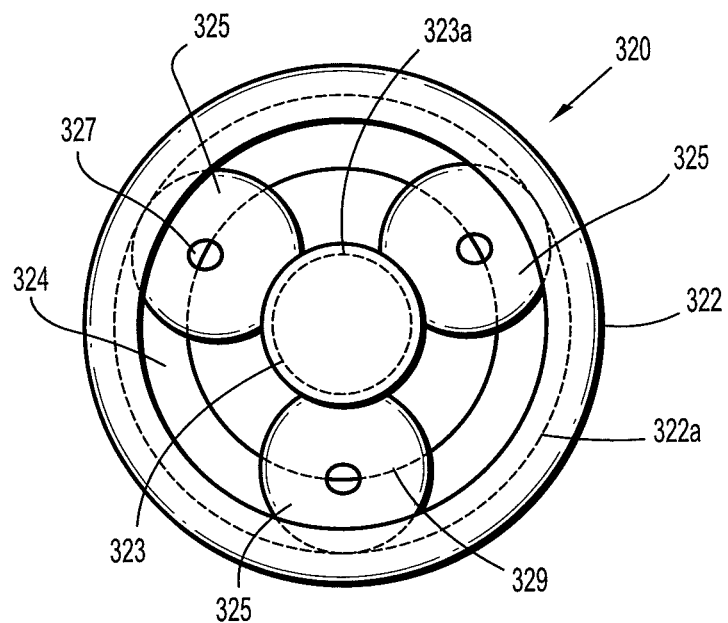
FIG. 10 is a top view of another embodiment of a seal member according to the present disclosure.

Turning initially to FIG. 10, a seal member 320 includes a rim 322, a hub 323 and an inner member 324 extending from hub 323. Inner member 324 is configured to ride within a groove 322a formed in rim 322 and groove 323a formed in hub 323. As shown, inner member 324 includes three first seal elements 325; however, it is envisioned that inner member 324 may include more or fewer first seal elements 325. Although shown formed as a single unit, each of first seal elements 325 formed in inner member 324 may instead be individually formed such that each first seal element 325 may be moved relative to each other. Each of first seal elements 325 is configured to receive an endoscopic instrument therethrough. Seal member 320 further includes a second seal element 327 formed from a flexible sheet and including a slit 329. Slit 329 is configured to receive an endoscopic instrument therethrough in a sealing manner. As with first and second seal elements 25, 37 described hereinabove with respect to seal members 20, 30, first and second seal elements 325, 327 operate to reduce leakage of insuflattion gases as endoscopic instruments "I1", "I2", inserted therethrough, are manipulated. Second seal element 327 may be affixed to rim 322, inner member 324 or may alternatively be formed as a second seal member.

Figure 11:
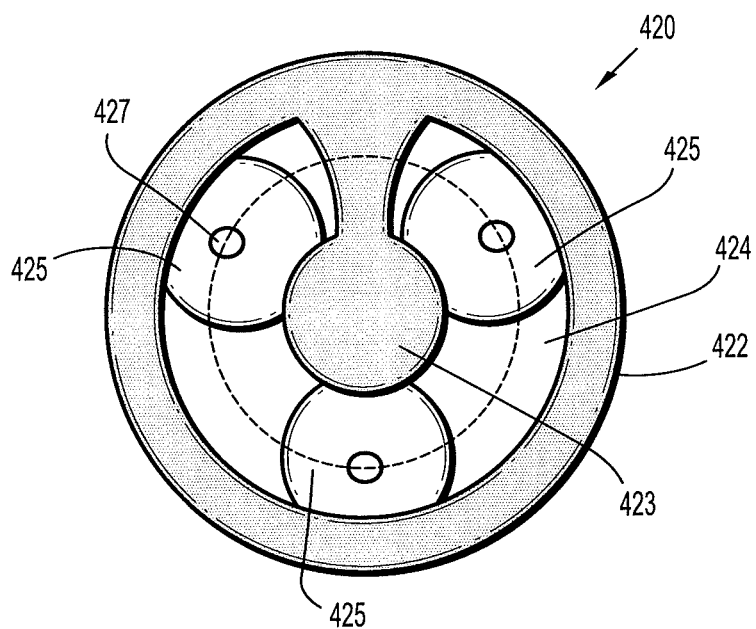
FIG. 11 is a top view of yet another embodiment of a seal member according to the present disclosure.

Turning now to FIG. 11, seal member 420 is substantially similar to seal member 320 and will only be described as relates to the differences therebetween. Seal member 420 includes rim 422, a hub 423 extending from rim 422, and an inner member 424 including first seal elements 425. Seal member 420 is configured such that inner member 424 may be rotated relative to rim 422 and hub 423. A second seal element 427 is attached to rim 422 and hub 423.

Figure 12:
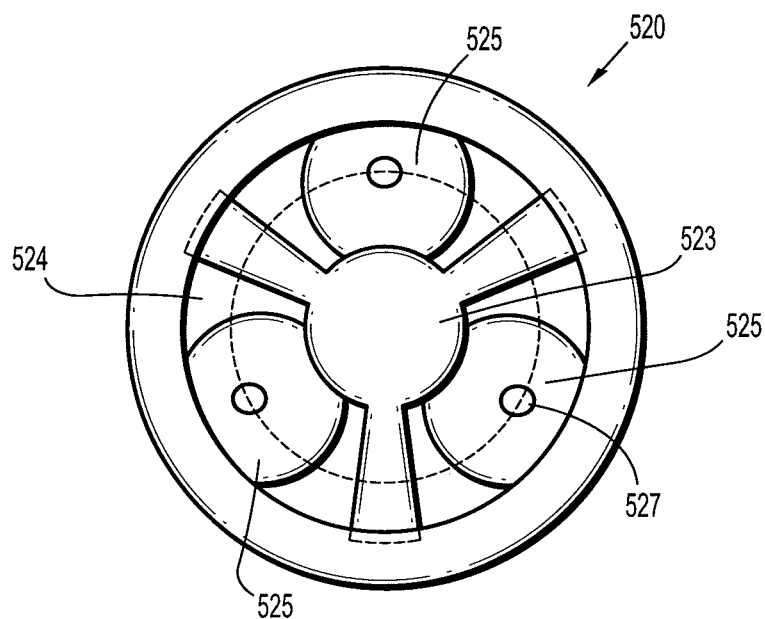
FIG. 12 is a top view of still another embodiment of a seal member according to the present disclosure.

With reference now to FIG. 12, seal member 520 includes a rim 522, a hub 523 and an inner member 524. Inner member 524 may be affixed to hub 523. Alternatively, inner member 524 may be configured to move independent of hub 523. Hub 523 includes extensions 523a configured to ride within a groove (not shown) formed in rim 522. Inner member 524 includes first seal elements 525. Seal member 520 further includes a second seal element 527.

Figure 13:
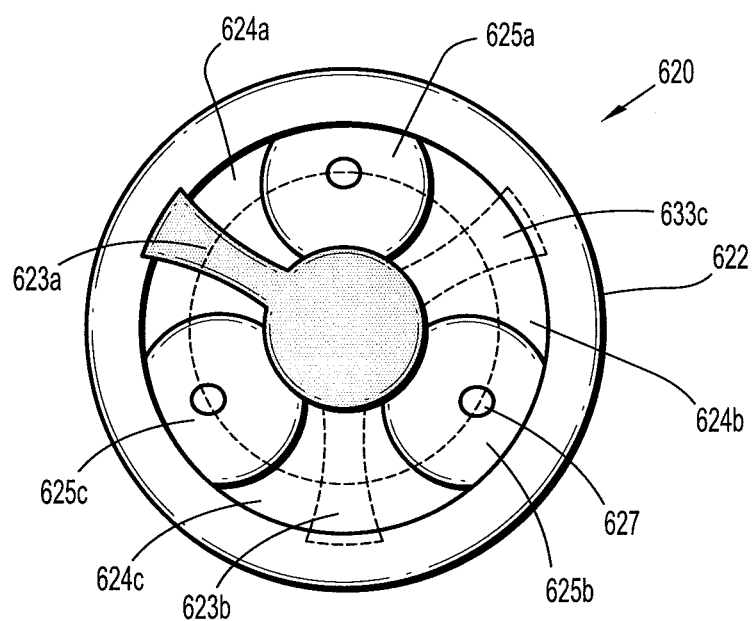
FIG. 13 is a top view of further embodiment of a seal member according to the present disclosure.

Turning now to FIG. 13, seal member 620 is substantially similar to seal member 520. Seal member 620 includes a rim 622, and first, second and third hub portion 623a, 632b, 623c, and corresponding inner members 624a, 624b, 624c. Although three hub portions are shown, it is envisioned that seal member 620 may include two or more hub portions. Hub portions 623a, 623b, 623c are configured to ride in independent grooves (not shown) formed in rim 622. Each inner member 624a, 624b, 624c corresponds to a first seal element 625a, 625b, 625c, respectively. Seal member 620 further includes a second seal element 627.

Figure 14:
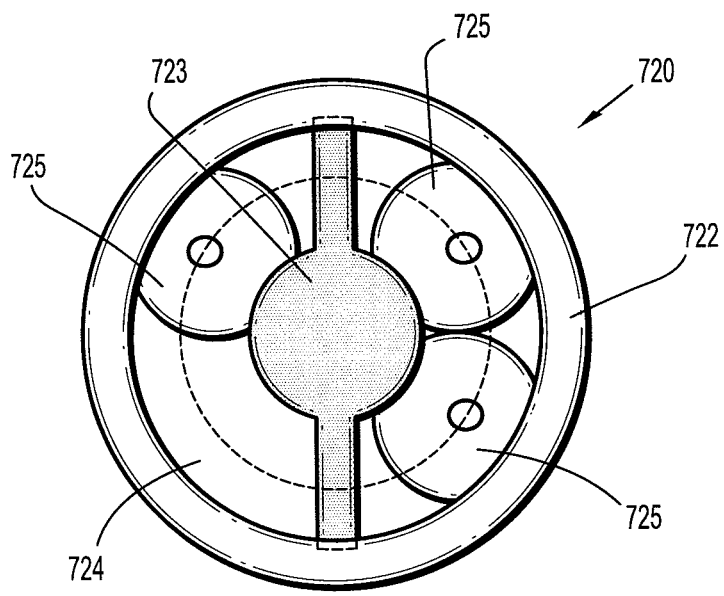
FIG. 14 is a top view of another embodiment of a seal member according to the present disclosure.

With reference now to FIG. 14, seal member 720 includes a rim 722, a hub 723 spanning rim 722 and an inner member 724 affixed to hub 723. Hub 723 and inner member 724 are configured to ride within a groove (not shown) formed in rim 722. Inner member 724 includes three first seal elements 725, although two or more seal elements may be included. Seal member 720 further includes a second seal element 727.

Figure 15:
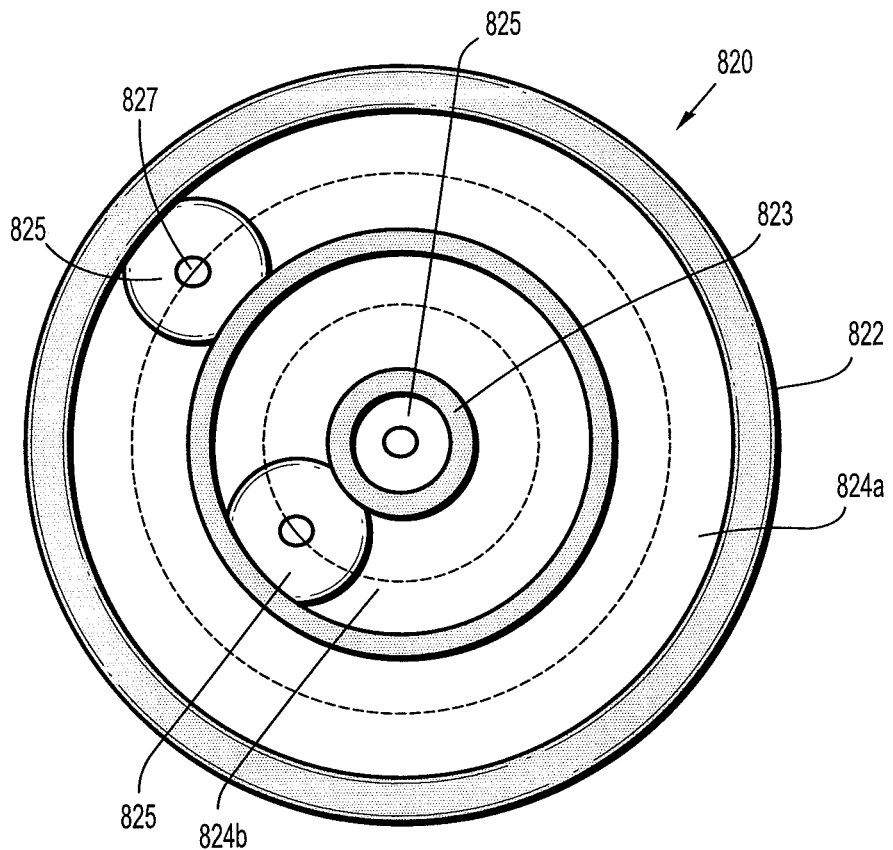
FIG. 15 is a top view of yet another embodiment of a seal member according to the present disclosure.

Turning now to FIG. 15, yet another embodiment of the present disclosure is shown generally as seal member 820. Seal member 820 includes a rim 822, a first inner member 824a, an inner ring 823a, a second inner member 824b, and a hub 823b. Each of first inner member 824a, second inner member 824b and hub 823b include a first seal element 825 and are configured to rotate relative to and independent of each other. Seal member 820 further includes at least a second seal element 827.

Although the illustrative embodiments of the present disclosure have been described herein with reference to the accompanying drawings, it is to be understood that the disclosure is not limited to those precise embodiments, and that various other changes and modifications may be effected therein by one skilled in the art without departing from the scope or spirit of the disclosure.

What is claimed is:

1. An access assembly, which comprises:
an access member defining a central longitudinal axis and having a longitudinal passageway therethrough for reception and passage of a surgical instrument, the access member dimensioned for positioning within tissue to provide access to an underlying site; and
first and second seal members mounted to the access member in juxtaposed relation, the first seal member having first internal surfaces defining an opening therethrough, the second seal member having second internal surfaces radially spaced from the central longitudinal axis and defining an elongated arcuate passage extending through an arc which subtends an angle greater than 0° with respect to the central longitudinal axis, the first and second seal members adapted for relative rotational movement about the central longitudinal axis whereby the opening of the first seal member is axially alignable with the elongated arcuate passage of the second seal member to permit passage and manipulation of the surgical instrument while establishing and maintaining a substantial sealed relation with the surgical instrument.

2. The access assembly according to claim 1 wherein the opening of the first seal member and the elongated arcuate passage of the second seal member are each radially spaced from the central longitudinal axis.

3. The access assembly according to claim 2 wherein the elongated arcuate passage of the second seal member is arranged to at least partially circumscribe the central longitudinal axis.

4. The access assembly according to claim 3 wherein the second seal member further includes an opening and the first seal member further includes an elongated arcuate passage whereby the opening of the second seal member is axially alignable with the elongated arcuate passage of the first seal member to permit passage and manipulation of a second surgical instrument while establishing and maintaining a substantial sealed relation with the surgical instrument.

5. The access assembly according to claim 4 including a third seal member mounted to the access member in juxtaposed relation with the second seal member, the third seal member including an opening and an elongated arcuate passage therethrough, the third seal member adapted for rotational movement about the central longitudinal axis.

6. The access assembly according to claim 5 wherein the third seal member is adapted for rotational movement relative to at least one of the first and second seal members.

7. The access assembly according to claim 4 wherein the elongated arcuate passage of each of the first and second seal members is dimensioned to extend through an arc which subtends an angle greater than 90° with respect to the central longitudinal axis.

8. The access assembly according to claim 7 wherein the elongated arcuate passage of each of the first and second seal members is dimensioned to extend through an arc which subtends an angle greater than 180° with respect to the central longitudinal axis.

9. An access assembly, which comprises:
an access member defining a central longitudinal axis and having a longitudinal passageway for reception and passage of surgical instruments, the access member dimensioned for positioning within tissue to provide access to an underlying site;
a first seal member mounted within the access member, the first seal member defining an opening and an elongated arcuate passage therethrough, each of the opening and the elongated arcuate passage being radially spaced from the central longitudinal axis;
a second seal member mounted within the access member in juxtaposed relation with the first seal member, the second seal member adapted for rotational movement about the central longitudinal axis relative to the first seal member and the access member, the second seal member defining an opening and an elongated arcuate passage therethrough, each of the opening and the elongated arcuate passage being radially spaced from the central longitudinal axis,
wherein the opening of the first seal member is axially alignable with the elongated arcuate passage of the second seal member to permit reception and passage of a first surgical instrument through both the opening of the first seal member and the elongated arcuate passage of the second seal member in substantial sealed relation with both the opening of the first seal member and the elongated arcuate passage of the second seal member, and the opening of the second seal member is axially alignable with the elongated arcuate passage of the first seal member to permit reception and passage of a second surgical instrument through both the opening of the second seal member and the elongated arcuate passage of the first seal member in substantial sealed relation with both the elongated arcuate passage of the first seal member and the opening of the second seal member.

10. The access assembly according to claim 9 wherein the elongated arcuate passage of each of the first and second seal members at least partially circumscribes the central longitudinal axis.

11. The access assembly according to claim 9 wherein the elongated arcuate passage of each of the first and second seal members is dimensioned to extend through an arc which subtends an angle greater than 90° with respect to the central longitudinal axis.

12. The access assembly according to claim 11 wherein the elongated arcuate passage of each of the first and second seal members is dimensioned to extend through an arc which subtends an angle greater than 180° with respect to the central longitudinal axis.

13. The access assembly according to claim 9 wherein the first seal member is adapted for rotational movement about the central longitudinal axis relative to the access member.

14. The access assembly according to claim 9 further including a third seal member mounted to the access member in juxtaposed relation with the second seal member, the third seal member including an opening and an elongated arcuate passage therethrough, the third seal member adapted for rotational movement about the central longitudinal axis.

15. The access assembly according to claim 14 wherein the third seal member is adapted for rotational movement relative to at least one of the first and second seal members.

16. The access assembly according to claim 9 wherein the opening in each of the first and second seal members includes a zero-closure seal.

17. The access assembly according to claim 9 wherein the elongated arcuate passage in each of the first and second seal members includes a slit seal.

18. The access assembly according to claim 9 wherein each of the first and second seal members includes overlapping portions within the elongated arcuate passage.

* * * * *